United States Patent [19]

Lincoln et al.

[11] Patent Number: 5,430,179
[45] Date of Patent: Jul. 4, 1995

[54] HOMOGENEOUS PROCESS FOR THE RUTHENIUM CATALYZED ADDITION OF CARBOXYLIC ACIDS TO ALKYNES

[75] Inventors: David M. Lincoln, Charleston; Rex E. Murray, Cross Lanes, both of W. Va.

[73] Assignee: Union Carbide Chemicals & Plastics Technology, Danbury, Conn.

[21] Appl. No.: 282,208

[22] Filed: Jul. 28, 1994

[51] Int. Cl.$^6$ .............................................. C07C 67/02
[52] U.S. Cl. ................... 560/261; 554/230; 560/1; 560/104; 560/95
[58] Field of Search .............. 560/261, 1, 95, 104; 554/230

[56] References Cited

U.S. PATENT DOCUMENTS

| | | | |
|---|---|---|---|
| 3,135,784 | 6/1964 | Feder | 260/476 |
| 3,455,998 | 7/1969 | Arpe | 260/498 |
| 3,574,717 | 4/1971 | Lloyd | 260/497 |
| 3,607,915 | 9/1971 | Borsboom et al. | 260/498 |
| 3,898,252 | 8/1975 | Serota et al. | 260/410.9 |

FOREIGN PATENT DOCUMENTS

| | | |
|---|---|---|
| 512656A2 | 5/1992 | European Pat. Off. . |
| 581501 | 10/1946 | United Kingdom . |
| 945028 | 12/1963 | United Kingdom . |
| 1013934 | 12/1965 | United Kingdom . |
| 1130245 | 10/1968 | United Kingdom . |
| 1125055 | 8/1969 | United Kingdom . |

OTHER PUBLICATIONS

Michal Rotem and Youval Shvo, Addition of Carboxylic Acids to Alkynes Catalyzed by Ruthenium Complexes. Vinyl Ester Formation, Organometallics 1983, 2, 1689–1691.

Take-aki Mitsudo, Yoji Hori, Yoshihisa Watanabe, Selective Addition of Unsaturated Carboxylic Acids to Terminal Acetylenes Catalyzed by Bis(n$^5$-cyclooctadieny)ruthenium(II)-Tri-n-butylphosphone. A Novel Synthesis of Enol Esters, J. Org. Chem. 1985, 50, 1566–1568.

Take-aki Mitsudo, Yoji Hori, Yasushi Yamakawa and Yoshihisa Watanabe, Ruthenium–Catalyzed Selective Addition of Carboxylic Acids to Alkynes. A Novel Synthesis of Enol Esters, J. Org. Chem., 1987, 52, 2230–2239.

Edward Rothman and Samuel Serota, Enol Esters XIII: Synthesis of Isopropenyl Esters by Addition to Carboxylic Acids to Propyne, Reprinted from the Journal of American Oil Chemists' Society, vol. 48, No. 8, pp. 373–375 (Aug. 1971).

*Primary Examiner*—Paul J. Killos
*Attorney, Agent, or Firm*—R. M. Allen; W. K. Volles

[57] ABSTRACT

The present invention relates to a homogeneous, ruthenium catalyzed liquid phase process for vinyl ester synthesis. It has been found that by adding at least one selectivity enhancer to the reaction system, selectivity to the addition reaction is improved while byproduct formation is inhibited. Useful selectivity enhancers include non-reacting heteroatom containing molecules that are believed to act by weakly coordinating to the ruthenium/phosphine ligand complex.

12 Claims, No Drawings

HOMOGENEOUS PROCESS FOR THE RUTHENIUM CATALYZED ADDITION OF CARBOXYLIC ACIDS TO ALKYNES

BACKGROUND OF THE INVENTION

This invention relates to a homogeneous, ruthenium catalyzed liquid phase process for vinyl ester synthesis. The process provides lower reaction temperatures and higher selectivity than prior zinc based acetylene routes and ruthenium based gas phase routes to vinyl esters.

The addition of carboxylic acids to acetylenically unsaturated compounds (i.e., alkynes) is known to be catalyzed by strong acids, Lewis acids, and electrophiles. The literature suggests that the preferred catalysts for vinylation reactions have been cadmium salts and zinc salts of the carboxylic acid in combination with a metal-containing Lewis acid. Gas phase reaction of acetylene and carboxylic acids has been accomplished in the presence of zinc and cadmium salts of the carboxylic acid, and mercury salts. Significant deficiencies in the use of this catalyst include toxicity concerns over the use of mercury and lack of selectivity and stability of zinc-based catalysts.

Ruthenium based catalysts have been found to promote the addition of carboxylic acids to alkynes and to produce alkenyl carboxylates. The reaction of carboxylic acids with acetylene (vinylation) to give vinyl esters is known to occur at a much slower rate and with lower selectivities to the desired vinyl esters. Various catalyst precursors have been studied to improve the rate of this reaction, including ruthenium carbonyl, bis(eta 5-cyclooctadienyl)ruthenium(II)/tri-n-butylphosphine, and bis(eta 5-cyclooctadienyl)ruthenium (II)/trialkylphosphine/maleic anhydride, ruthenium trichloride, ruthenium dicarbonyl bis-triphenylphosphine acetate dimer, and ruthenium tricarbonyl bis-triphenylphosphine.

The major by-product in the ruthenium catalyzed reaction of acetylenically unsaturated compounds with carboxylic acids is the carboxylic acid anhydride. In many cases, the rate of anhydride formation is equal to or greater than the rate of-vinyl ester formation.

Attempts to control by-product formation include the use of phosphine ligands to inhibit anhydride formation and increase vinyl ester selectivity, and removal of the vinyl ester product.

Another problem associated with the use of ruthenium catalyst in these reactions is catalyst stability. In general, catalyst stability is moderate and is dependent on the presence of ruthenium/phosphine ligand complexes. Two potential routes of deactivation include phosphine ligand oxidation and ruthenium cluster formation.

The use of ruthenium compositions as vinylation catalysts has overcome several of the deficiencies of the prior art, however; the need exists for a homogeneous liquid phase process for the production of vinyl esters, which provides higher selectivity at lower temperatures; with minimal catalyst degradation.

SUMMARY OF THE INVENTION

The present invention provides a homogeneous, liquid phase process for vinyl ester synthesis, which comprises reacting a carboxylic acid with an alkyne in the presence of a ruthenium/phosphine ligand catalyst complex, and at least one selectivity enhancer. It is believed that the selectivity enhancers improve selectivity of the addition reaction for the production of the vinyl ester and reduce byproduct, anhydride formation.

Useful selectivity enhancers include non-reacting heteroatom containing molecules that are believed to act by weakly coordinating to the ruthenium/phosphine ligand catalyst complexes, thereby reducing the ruthenium catalyzed rate of anhydride formation to a greater degree than the rate of ruthenium catalyzed carboxylic acid addition to acetylene; resulting in an enhanced rate of reaction and selectivity to the desired vinyl ester.

Catalyst stability has been found to be improved by the use of these selectivity enhancers.

DETAILS OF THE INVENTION

Acetylenically unsaturated compounds typically used in the process of the present invention include alkynes that may be unsubstituted or substituted with one or more substituents not interfering with the addition reaction. Representative substituents include alkyl, alkoxy, aryl, aryloxy, acetoxy, carboxyl and halo groups. Alkynes typically have from 2 to 10 carbon atoms and preferred alkynes include substituted or unsubstituted primary alkynes such as acetylene, methyl acetylene, phenyl acetylene, 1-butyne, 1-pentyne, 1-hexyne, 1-heptyne, 1-octyne, 1-nonyne, 1-decyne and the like. Preferred alkynes useful in the practice of the invention include acetylene and methyl acetylene.

Illustrative of suitable carboxylic acids for the practice of the invention are monocarboxylic and polycarboxylic acids illustrated by acetic acid, propionic acid, butyric acid, valetic acid, hexanoic acid, heptanoic acid, octanoic acid, nonanoic acid, decanoic acid, 2-methylpropionic acid, 2-methylbutyric acid, 3-methylbutyric acid, 2-methylpentanoic acid, 2-ethylhexanoic acid, 2-propyl heptanoic acid; pivalic acid and other neo acids such as neodecanoic acid, neotridecanoic acid and neononanoic acid; stearic acid, fatty acids, benzoic acid, terephthalic acid, isophthalic acid, phthalic acid, adipic acid, succinic acid, malic acid, maleic acid, polyacrylic acids, crotonic acid, acrylic acid, methacrylic acid, salicylic acid, cinnamic acid, and cyclohexanoic acid.

The process of this invention provides an excellent route to many hard to produce vinyl compounds because of the desirable physical and chemical properties of the ruthenium compounds that provide the basis for the catalic reaction. The ruthenium catalysts are easily obtainable as soluble components and can be used in the form of non-volatile compounds possessing high thermal stability.

The selection of a suitable ruthenium compound to provide the catalytic activity for the vinylation reaction is not narrowly critical. The exact ruthenium containing compound or compounds that constitute the catalysts of this invention is not appreciated but what is appreciated is that many ruthenium compounds can be used to in situ generate the catalyst.

The most preferred catalyst precursors are derived from ruthenium carbonyl carboxylates, or other ruthenium compounds that can convert into these species. Illustrative of such compounds include ruthenium carbonyl, ruthenium dicarbonylacetate, ruthenium dodecacarbonyl, ruthenium chloride, dicarbonylcyclopentadienylruthenium (II) dimer, dichloro(1,5-cyclooctadiene) ruthenium (II), dichlorodicarbonylbis (trialkylphosphine)ruthenium (II), dichlorotricarbonyl ruthenium (II) dimer, ruthenium (III) acetylacetonate, and dichlorotris(trialkylphosphine) ruthenium (II). Additional catalyst precursors useful in the practice of the present invention include those disclosed in U.S. Patent 4,981,973, incorporated herein by reference.

Based on the recognition that ruthenium carbonyl reacts with carboxylic acids to produce soluble orange-yellow complexes possessing the empirical formula $[Ru(CO)_2RCO_2]_n$, it is believed that such structures are involved in the catalysis of the vinylation process. The presumed catalyst precursor, $[Ru(CO)_2RCO_2]_n$, can be generated in several ways. For example the trinuclear complex, $[Ru_3O(OAc)_6(H_2O)_3]OAc$, gives an efficient vinylation catalyst. Infrared analysis indicates that $[Ru_3O(OAc)_6(H_2O)_3]OAc$, can convert to $[Ru(CO)_2RCO_2]_n$ under vinylation reaction conditions.

Preferred ruthenium carbonyl catalyst complexes include those based on ruthenium dicarbonyl carboxylate/phosphine complexes. When the ruthenium compound already contains a phosphine ligand, these compounds may be used alone in the process or with additional phosphine ligands. Useful phosphine ligands for forming the ruthenium/phosphine catalyst complex include both alkyl and aryl phosphines. Phosphorus ligands useful in the present invention include those having the formula:

$$P(X)_3$$

where X is selected from the group hydrogen, $-C_6R_5$, and $-[(CR_2)_{0-n}CR_3]$; R is one of more of hydrogen, straight chain hydrocarbon, branched hydrocarbon, phenyl, substituted phenyl, halogen, alkoxy, cyano, carboxyl, carbamyl, amino, and phosphoryl; and n is 1-25.

Illustrative of such ligands include trimethyl phosphine, triethyl phosphine, tripropyl phosphine, triisopropyl phosphine, tributyl phosphine, tri-t-butyl phosphine, triphenyl phosphine, tris(2-cyanoethyl)phosphine, tris(methoxyphenyl)phosphine, tris(p-fluoromethylphenyl)phosphine, tritolylphosphine, tricyclohexylphosphine, dicyclohexylphenylphosphine, diphenylcyclohexylphosphine and the like. Alkylphosphines are preferred over arylphosphines.

In addition, phosphorous ligands that serve as a combination of phosphorous ligand and selectivity enhancer may be used and include those having the formula:

$$(X)_aP-(Y-Z)_b$$

where X is selected from the group hydrogen, $-C_6R_5$, and $-[(CR_2)_{0-n}CR_3]$, R is one or more of hydrogen, straight chain hydrocarbon, branched hydrocarbon, phenyl, substituted phenyl, halogen, alkoxy, cyano, carboxyl, carbamyl, amino, phosphoryl, Y is $(CR_2)n$ and Z is a selectivity enhancer, as herein described; a is 0-2, b is 1-3, with a+b=3, and n is 1-25.

It has been found that the selectivity enhancers of the present invention coordinate weakly to the ruthenium/phosphine catalyst complex to improve reaction selectivity to the vinyl ester product and inhibits anhydride formation. Although the exact mechanism is not understood, it is believed that these selectivity enhancers inhibit coordination of the vinyl ester product with the ruthenium/phosphine catalyst complex, impeding ruthenium coordinated vinyl ester reaction with carboxylic acid to form carboxylic anhydride and acetaldehyde. Illustrative of such compounds include tetrahydrofuran, acetonitrile, carbon monoxide and other non-reacting heteroatom containing compounds such as dioxanes, thiophenes, ethers, cyclic ethers, crown ethers, furans, and pyrans, including substituted higher molecular weight, less volatile derivatives of the same.

The amount of ruthenium catalyst useful for effecting the vinylation reaction is not narrowly critical. The typical amount is a catalytically effective amount, that is, an amount sufficient to effect the desired vinyl ester production. In the practice of the present invention, it is desirable to maintain an adequate ruthenium concentration to promote a rapid vinylation rate. For example, ruthenium catalyst concentrations ranging roughly from about 50,000 parts to about 0.5 part per million (ppm) ruthenium based on the weight of the liquid phase reaction medium can be used to effect the reaction. Catalyst concentrations in the range of from about 100 ppm to about 10,000 ppm ruthenium relative to the total charged reactants and solvents in the reactor are more preferred. The most preferred range is from about 500 ppm to about 5,000 ppm ruthenium, same basis. It will be appreciated that the catalyst concentration can be optimized depending on the vinyl ester to be made, reaction temperature, and the like.

It is desirable that the vinylation reaction be carried out in the absence of an amount of water in the reaction mixture that inhibits the production of the desired vinyl ester product. However, as shown in the Examples below, the reaction can be carried out in the presence of small quantities of water without detrimental effects. Improved selectivity may be obtained in the presence of water due to the in situ hydrolysis of the byproduct anhydride to the starting carboxylic acid. As a rule, the amount of water present in the reaction is desirably less than about 5 weight percent of the weight of the reaction mixture. Preferably, the amount of water in the reaction is less than about 3 weight percent of the weight of the mixture.

It is desirable to operate at a temperature at which the acid reactant is dissolved or liquid. The process is favorably effected by keeping the reaction temperature below the boiling point of the highest boiling reactant or at sufficient pressure to maintain the liquid state. When feasible, the liquid phase condition can best be accomplished by operating at temperatures above the melting point of the acid. Overall, the temperatures at which these reactions may be carried out are safer and much lower than other liquid or gas phase vinylation processes. Suitable ranges are from about 40° C. to about 200° C., preferably from about 80° C. to about 120° C., and most preferably from about 90° C. to about 110° C.

The optimum reaction conditions depend chiefly on the carboxylic acid to be vinylated. If the acid is soluble at the reaction temperature, it better to operate without solvent. However, non-coordinating solvents such as toluene, heptane, silicone oil, mineral oil, phenyl ether, phenyl benzoate, methyl benzoate, dimethylterephthalate, and dioctylphthalate may be used. Coordinating solvents tend to inhibit vinylation reaction rates, but may find usefulness as a selectivity enhancer when used at lower concentrations as discussed below.

The process of the present invention is operational over a broad range of mole ratios of carboxylic acid to acetylene. In general, ratios of about 100/1 to about 1/100 are preferred and ratios of about 1/10 to about 10/1 are most preferred. The mole ratio of ligand to ruthenium is preferred to be from about 10:1 to about 1.1:1, ligand to metal. Higher concentrations of ligand tend to inhibit the reaction and may completely stop the reaction at significantly higher concentrations. The selectivity enhancer may be present in ratios of from about 1:1 selectivity enhancer to ruthenium to about 100,000:1 selectivity enhancer to ruthenium. Molecules that coordinate more strongly to the ruthenium/phosphine ligand catalyst complexes tend to give better results at lower concentrations than do more weakly coordinating molecules. In a preferred embodiment, maximum rates and selectivities may be achieved with ruthenium dicarbonyl acetate precursor catalyst, one equivalent of tributylphosphine ligand and 100 equivalents of tetrahydrofuran as a selectivity enhancer (both equivalents based on ruthenium).

Several reaction atmospheres, such as air, nitrogen, ethylene, ethane, propane, propylene and other volatile hydrocarbons are compatible with the vinylation catalyst. The most preferred reaction pressure is less than about 15 psig, due to safety concerns. However, when special provisions are made to reduce the danger of explosion, higher pressures, which are preferred, may also be used.

The reaction is preferably carried out under conditions at which all of the reactants are in the liquid phase. This does not require that the reaction environment be wholly in the liquid phase, as acetylene is normally a gas at these temperatures and pressures. It simply means that a sufficient amount of the reactants and the catalyst may be in the liquid phase such that the reaction can occur in the liquid phase. For example, solid ruthenium on a solid support can be used as a catalyst precursor. In the presence of reactant, solvent and/or selectivity enhancers, sufficient solid ruthenium may be converted to a liquid soluble compound such that the catalytic reaction is attainable.

The vinyl esters are separated from the liquid reaction medium by conventional methods including distillation, evaporation, fractionation, solvent extraction and the like. Vinyl esters prepared by the process of the present invention include, for example, vinyl acetate, vinyl propionate, vinyl butyrate, vinyl valerate, vinyl hexanoate, vinyl heptanoate, vinyl octanoate, vinyl nonanoate, vinyl decanoate, vinyl 2-methyl propionoate, vinyl 2-methylbutyrate, vinyl 3-methylbutyrate, vinyl 2-methylpentanoate, vinyl 2-ethylhexanoate, vinyl 2-propylheptanoate, vinyl pivalate, vinyl neodecanoate, vinyl neotridecanoate, vinyl neononanoate, vinyl stearate, vinyl benzoate, and the like.

GLOSSARY OF TERMS

The following abbreviations and meanings are used in the examples:

| | |
|---|---|
| ACN | Acetonitrile |
| CO | Carbon Monoxide |
| DIPHOS | 1,2-bis(diphenylphosphino)ethane |
| MA | Maleic Anhydride |
| PYR | Pyridine |
| THF | Tetrahydrofuran |

EXAMPLES

Catalytic activity of various ruthenium/phosphine ligand catalyst complexes and selectivity enhancers is evaluated according to the following procedure. A mixture of ruthenium dicarbonyl acetate (1000 ppm Ru), pivalic acid (25 grams), a specified amount of phosphine ligand (1 equivalent), and a specified amount of at least one selectivity enhancers is charged to a 3 oz. Fischer-Porter bottle, sealed and heated at 100° C. for 30 minutes (catalyst preparation period). The vessel is then pressurized to 10 psig acetylene, purged and subjected to a constant 15 psig pressure of acetylene. The magnetically stirred reaction mixture is heated in an oil bath to 100° C. for a period of time from 6 to 70 hours. Periodic gas chromatographic analysis on a DB-1 fused silica capillary column (30M) reveals the amount of vinyl pivalate formed by the vinylation process. Selectivity to vinyl pivalate is defined by the number of moles of vinyl pivalate produced per number of moles pivalic acid consumed.

Examples 1–15 (Table I) show the effect of various selectivity enhancers in systems with triglyme as a solvent.

TABLE I

| Ru, g | Phosphine | Additive, g | Vinyl Pivalate Selectivity |
|---|---|---|---|
| 0.065 | Tris(pentafluorophenyl) | 0 | 29% |
| 0.065 | Tris (p-fluorophenyl) | 0 | 21% |
| 0.065 | Tri-p-chlorophenyl | 0 | 20% |
| 0.065 | Tri-m-chlorophenyl | 0 | 29% |
| 0.065 | Tributyl | 0 | 50% |
| 0.065 | DIPHOS | 0 | 53% |
| 0.065 | Triphenyl | 0 | 35% |
| 0.065 | Triphenyl | CO, 5 psi | 38% |
| 0.065 | Triphenyl | CO, 10 psi | 38% |
| 0.065 | Triphenyl | MA, 0.03 | 23% |
| 0.065 | Triphenyl | MA, 0.14 | 27% |
| 0.065 | Triphenyl | MA, 1.0 | 12% |
| 0.065 | Triphenyl | PYR, 0.023 | 25% |
| 0.065 | Triphenyl | PYR, 0.12 | 20% |
| 0.065 | Triphenyl | PYR, 1.0 | 17% |

Examples 16–29 (Table II) shows the effect of various selectivity enhancers in systems without the use of solvent. In addition, the effects of adding water to the reaction mixture is demonstrated.

TABLE II

| Ru, g | Phosphine | Additive, g | Vinyl Pivalate Selectivity |
|---|---|---|---|
| 0.030 | None | 0 | 5% |
| 0.030 | Tributyl | 0 | 74% |
| 0.065 | Tributyl | 0 | 78% |
| 0.065 | Tributyl | THF, 0.022 | 70% |
| 0.065 | Tributyl | THF, 0.22 | 75% |
| 0.065 | Tributyl | THF, 2.2 | 92% |
| 0.130* | Tributyl | THF, 22 | 45% |
| 0.130* | Tributyl | THF, 4.4 | 81% |
| 0.130* | Tributyl | THF, 4.4; H2O, 1.0 | 98% |
| 0.065 | DIPHOS | 0 | 41% |
| 0.130* | DIPHOS | ZHF, 4.4 | 87% |
| 0.065 | Tributyl | ACN, 0.014 | 78% |
| 0.065 | Tributyl | ACN, 0.14 | 59% |

*Reactions were run in a 6 oz. Fischer-Porter Vessel.

What is claimed is:

1. A homogeneous, liquid phase process for vinyl ester synthesis which comprises reacting a carboxylic acid with an alkyne in the presence of a ruthenium/phosphine ligand catalyst complex, and at least one selectivity enhancer.

2. The process of claim 1 wherein the carboxylic acid is selected from the group consisting of acetic acid, propionic acid, butyric acid, valeric acid, hexanoic acid heptanoic acid, octanoic acid, nonanoic acid, decanoic acid, 2-methylpropionic acid, 2-methylbutyric acid, 3-methylbutyric acid, 2-methylpentanoic acid, 2-ethylhexanoic acid, 2-propyl heptanoic acid; pivalic acid and other neo acids such as neodecanoic acid, neotridecanoic acid and neononanoic acid; stearic acid, fatty acids, benzoic acid, terephthalic acid, isophthalic acid, phthalic acid, adipic acid, succinic acid, malic acid, maleic acid, polyacrylic acids, crotonic acid, acrylic acid, methacrylic acid, salicylic acid, cinnamic acid, and cyclohexanoic acid.

3. The process of claim 1 wherein the alkyne is selected from the group consisting of acetylene, methyl acetylene, phenyl acetylene, 1-butyne, 1-pentyne, 1-hexyne, 1-heptyne, 1-octyne, 1-nonyne, and 1-decyne.

4. The process of claim 1 wherein the ruthenium/phosphine ligand catalyst complex is derived from a ruthenium compound selected from the group consisting of ruthenium carbonyl, ruthenium dicarbonylacetate, ruthenium dodecacarbonyl, ruthenium chloride, dicarbonylcyclopentadienyl ruthenium (II) dimer, dichloro(1,5-cyclooctadiene) ruthenium (II), dichlorodicarbonylbis (trialkylphosphine)ruthenium (II), dichlorotricarbonyl ruthenium (II) dimer, ruthenium (III) acetylacetonate, and dichlorotris(trialkylphosphine) ruthenium (II).

5. The process of claim 1 wherein the phosphine ligand of the ruthenium/phosphine ligand catalyst complex has the structure:

$$P(X)_3$$

where X is selected from the group hydrogen, $-C_6R_5$, and $-[(CR_2)_{0-n}CR_3]$; R is one of more of hydrogen, straight chain hydrocarbon, branched hydrocarbon, phenyl, substituted phenyl, halogen, alkoxy, cyano, carboxyl, carbamyl, amino, and phosphoryl; and n is 1–25.

6. The process of claim 1 wherein the phosphine ligand of the ruthenium/phosphine ligand catalyst complex has the structure:

$$(X)_aP-(Y-Z)_b$$

where X is selected from the group hydrogen, $-C_6R_5$, and $-[(CR_2)_{0-n}CR_3]$, R is one of more of hydrogen, straight chain hydrocarbon, branched hydrocarbon, phenyl, substituted phenyl, halogen, alkoxy, cyano, carboxyl, carbamyl, amino, phosphoryl, Y is $(CR_2)_n$ and Z is a selectivity enhancer, as herein described; a is 0–2, b is 1–3, with a+b=3, and n is 1–25.

7. The process of claim 1 wherein the ruthenium/phosphine ligand catalyst complex contains a phosphine ligand selected from the group consisting of trimethyl phosphine, triethyl phosphine, tripropyl phosphine, triisopropyl phosphine, tributyl phosphine, tri-t-butyl phosphine, triphenyl phosphine, tris(2-cyanoethyl)phosphine, tris(methoxyphenyl )phosphine, tris(p-fluoromethylphenyl )phosphine, tritolylphosphine, tricyclohexylphosphine, dicyclohexylphenylphosphine, and diphenylcyclohexylphosphine.

8. The process of claim 1 wherein the selectivity enhancer is selected from the group consisting of tetrahydrofuran, acetonitrile, carbon monoxide, dioxanes, thiophenes, ethers, cyclic ethers, crown ethers, furans, and pyrans, including substituted higher molecular weight, less volatile derivatives of the same.

9. The process of claim 1 wherein the temperature ranges from about 40° C. to about 200° C., preferably from about 80° C. to about 120° C., and most preferably from about 90° C. to about 110° C.

10. The process of claim 1 wherein the selectivity enhancer is present in an amount from about 1:1 selectivity enhancer to ruthenium to about 100,000:1 selectivity enhancer to ruthenium.

11. The process of claim 1 wherein water is added in an amount of less than about 5 weight percent of the weight of the reaction mixture.

12. A homogeneous, liquid phase process for vinyl ester synthesis which comprises reacting pivalic acid with acetylene in the presence of a ruthenium dicarbonyl acetate/tributylphosphine ligand catalyst complex and tetrahydrofuran.

* * * * *